United States Patent [19]

Ijuin

[11] Patent Number: 5,131,847
[45] Date of Patent: Jul. 21, 1992

[54] DENTAL CROWN AND METHOD FOR MAKING SAME

[75] Inventor: Toshihiko Ijuin, Skokie, Ill.

[73] Assignee: Ijuin Dental Laboratory Inc., Ill.

[21] Appl. No.: 682,572

[22] Filed: Apr. 8, 1991

[51] Int. Cl.$^5$ .............................................. A61C 5/10
[52] U.S. Cl. ................................................... 433/223
[58] Field of Search ............ 433/218, 206, 208, 222.1, 433/223, 227

[56] References Cited

U.S. PATENT DOCUMENTS

| | | | |
|---|---|---|---|
| Re. 33,099 | 10/1989 | Shoher | 433/222.1 |
| Re. 33,271 | 7/1990 | Shoher | 433/222.1 |
| 1,431,425 | 10/1952 | Richmond . | |
| 1,457,370 | 6/1923 | Jeffries . | |
| 1,465,472 | 8/1923 | Hansen | 433/223 |
| 1,609,550 | 12/1926 | Jaques | 433/218 |
| 3,601,895 | 8/1971 | Zollner . | |
| 3,916,525 | 11/1975 | Hirsch . | |
| 4,062,676 | 12/1977 | Knosp . | |
| 4,104,798 | 8/1978 | Takahashi . | |
| 4,132,830 | 1/1979 | Tsai | 428/450 |
| 4,181,757 | 1/1980 | Youdelis | 427/229 |
| 4,214,356 | 7/1980 | Takenaka | 433/218 |
| 4,273,580 | 6/1981 | Shoher | 433/207 |
| 4,358,271 | 11/1982 | Sperner | 433/201 |
| 4,392,829 | 7/1983 | Tanaka | 433/222 |
| 4,426,404 | 1/1984 | Shoher | 427/2 |
| 4,459,112 | 7/1984 | Shoher | 433/222 |
| 4,461,618 | 7/1984 | DeLuca | 433/200 |
| 4,492,579 | 1/1985 | Shoher | 433/222 |
| 4,676,751 | 6/1987 | Shoher | 433/222 |
| 4,838,790 | 6/1989 | Koller | 433/222.1 |
| 4,861,267 | 8/1989 | Shoher | 433/218 |
| 4,940,637 | 7/1990 | Shoher | 428/607 |

FOREIGN PATENT DOCUMENTS

| | | |
|---|---|---|
| 3742967 | 6/1989 | Fed. Rep. of Germany ...... 433/218 |
| 3826664 | 2/1990 | Fed. Rep. of Germany ...... 433/223 |
| 8536 | 6/1890 | United Kingdom ................ 433/218 |

OTHER PUBLICATIONS

Mazulewicz, *Dental Laboratory Technology*, Department of the Air Force, AFM 162-6, Nov. 15, 1982, pp. 477–482.

Williams Dental Company, Inc., *Renaissance Crown Plus*, Jul. 1987.

Williams Dental Company, Inc., *Renaissance Crown Update*, Dec. 1986.

*Primary Examiner*—Cary E. O'Connor

[57] ABSTRACT

A method for making a jacket crown restoration is disclosed wherein the crown has a metal foil substrate of a high fusing temperature metal such as platinum as an integral component of the finished porcelain jacket crown. The present invention provides both anterior and posterior porcelain metal crown restorations and methods for making same. According to the present invention, a thin metal foil of a high fusing temperature metal is molded around a die of the tooth to be replaced. The foil has two ends which are terminated in a bondable mechanical joint to form a sealed thin metal foil substrate or skeleton for the dental preparation. The foil substrate is appropriately cleaned, coated with a retention compound to enhance the bonding of a veneer to the foil substrate and thereafter coated with a veneer to form the dental jacket crown.

25 Claims, 3 Drawing Sheets

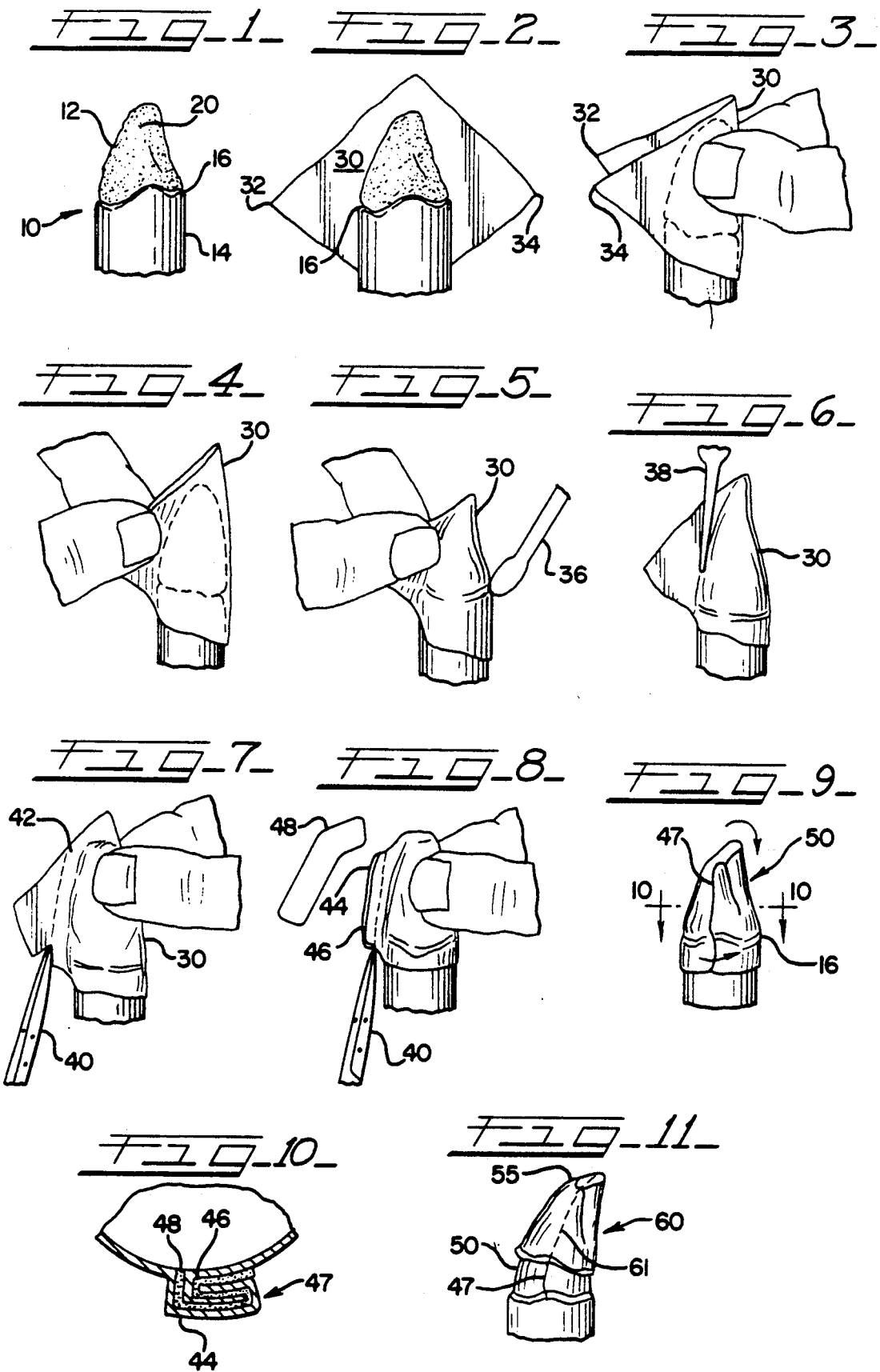

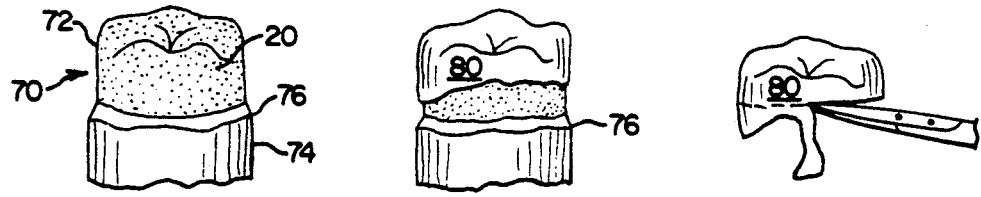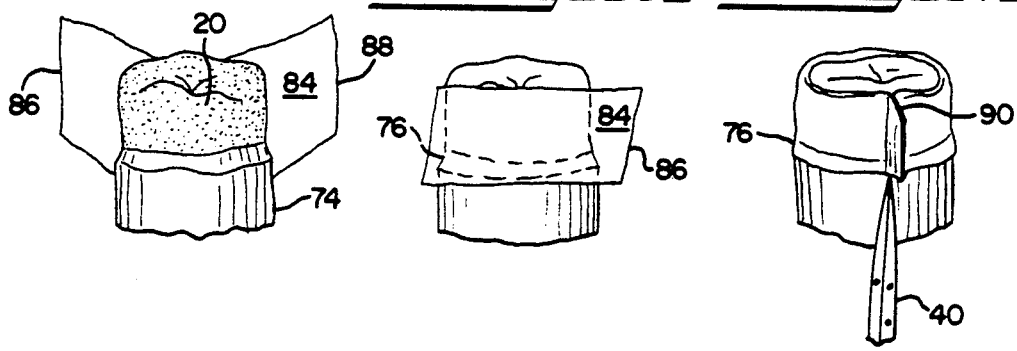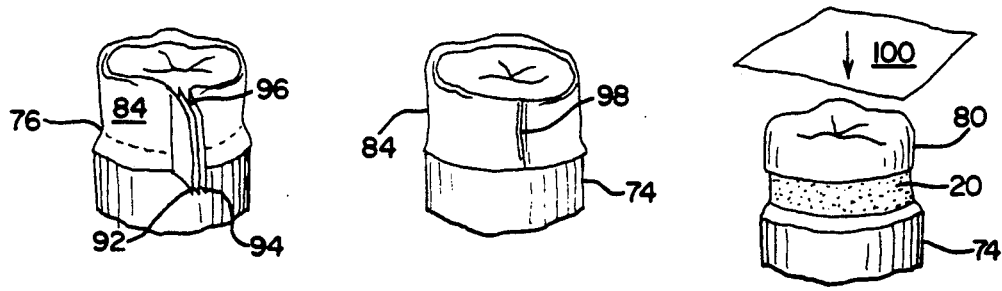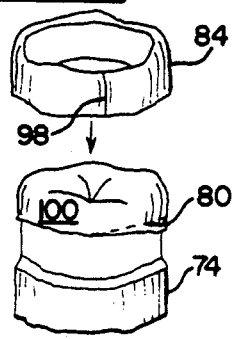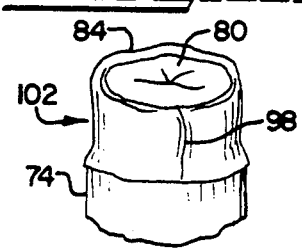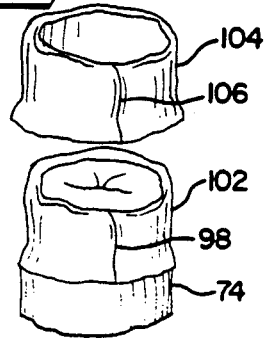

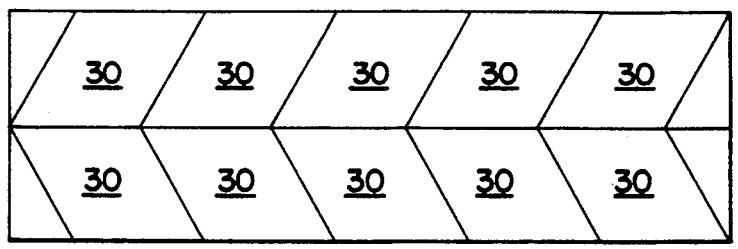
FIG_24_
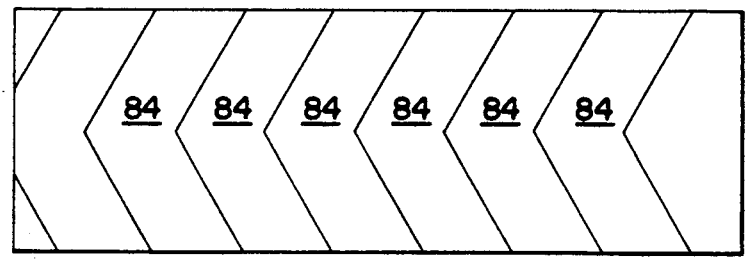
FIG_25_
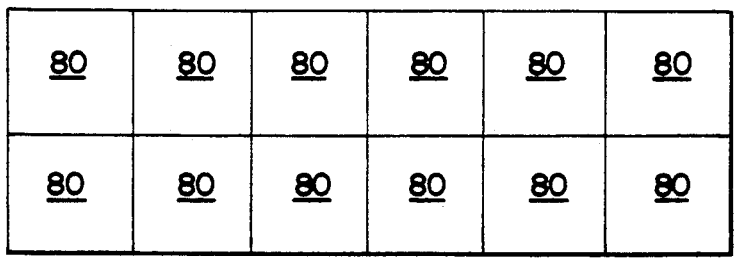
FIG_26_
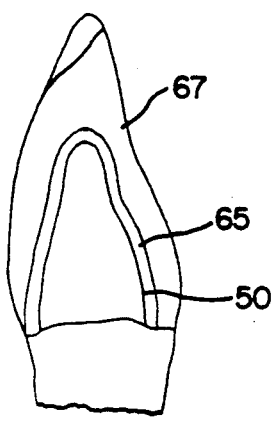
FIG_27_

DENTAL CROWN AND METHOD FOR MAKING SAME

BACKGROUND OF THE INVENTION

The present invention relates generally to the field of dental restorations and more particularly to porcelain crown restorations which utilize a thin metal foil as a substrate and to a method of making same.

Dental porcelain is commonly used in fabricating dental restorations. Porcelain restorations can be fabricated to approximate the natural tooth shading of the intended user and thereby provide a user with an aestheticly appealing replacement. Additionally, porcelain may be contoured to form a prescribed occlusal surface, is durable in saliva, has reduced thermal conductivity and resists abrasion from food and brushing.

Porcelain jacket crowns fell into disfavor for sometime because the use thereof required the dentist to grossly cut down a natural tooth and because the older feldspar porcelains tended to fracture. Improved formulations and methods for preparing porcelain crowns have since greatly enhanced the dependability and popularity of porcelain restorations.

One common method for preparing a porcelain jacket crown includes preparing a platinum foil matrix conforming to the shape which the restored tooth is to take and applying a porcelain cover, or jacket, onto the matrix. Typically, a porcelain jacket crown of this type will include a build-up of several layers of porcelain containing different concentrations of aluminum oxide (alumina). After the crown is formed to its "in-mouth" configuration, the platinum matrix is then removed from the crown before the crown is secured into the patient's mouth.

Another method for preparing porcelain crowns includes chemically bonding or fusing the porcelain to a metal substrate. For example, U.S. Pat. No. 4,273,580 is directed to a jacket crown formed of a composite body having an inner structure composed of a thin metal foil of platinum conforming in shape to the tooth preparation to be restored, at least one thin intermediate coating of a predetermined composition of finely divided particles bonded to the thin metal foil and a relatively thick fired-on outer coating of dental porcelain. The intermediate coating of the '580 patent comprises from about 1 to 100% by weight of a noble metal chloride selected from a specified group in combination with from 0 to 99% by weight of a gold based noble metal. According to the '580 patent, it is essential that the intermediate coating is bonded to the thin metal foil at an elevated sintering temperature of at least 1600° F.

U.S. Pat. No. 4,392,829 is directed to a baked metal-porcelain dental restoration having a non-cast thin metal foil substrate. The surface of the foil substrate is textured and is capable of bonding directly to dental porcelain when baked without any intermediate interface compositions. According to the '829 patent, the porcelain layer is bonded directly to the textured surface and the exterior of the porcelain may be configured as prescribed. The metal substrate, however, is not sealed and the crown therefore is not fully protected against migration of fluids and contaminants.

U.S. Pat. No. 4,459,112 and its related patents, e.g. RE33,099, No. 4,492,579 and RE33,271, disclose jacket crown restorations wherein a metal foil substrate serves as an integral component of the finished porcelain jacket crown. The disclosed foil substrate is preferably circular in geometry and is composed of a thin foil metal base of platinum or another high fusing temperature metal and a thin coated layer superimposed on the base metal. The coated layer is indicated to be a noble metal base composition preferably with gold as its major constituent. The metal foil is folded into a predetermined geometrical shape having a multiple number of fold lines for forming a dental coping. The coping is adapted to a die and heat treated to sinter the overlapping folds to one another. In addition to requiring a special foil, this method produces multiple pleats (joint lines) in the substrate structure which are undesirable.

SUMMARY OF THE INVENTION

In accordance with the present invention, a jacket crown restoration is formed as a composite body having a metal foil substrate of a high fusing temperature metal such as platinum as an integral component of the finished porcelain jacket crown. The present invention provides both anterior and posterior porcelain metal crown restorations According to the present invention, a thin metal foil of a high fusing temperature metal is molded around a die of the tooth to be replaced. The foil has two ends which are terminated in a bondable mechanical joint to form a sealed thin metal foil substrate or skeleton for the dental preparation. In an alternate embodiment of the present invention a unitary thin metal substrate is prepared from an occlusal metal foil member and a facial metal foil member bonded together. The foil substrates of the present invention are appropriately cleaned, coated with a retention compound to enhance the bonding of a veneer to the foil substrate and thereafter coated with a veneer to form dental jacket crowns.

Accordingly, it is a general object of the present invention to provide an improved method of making a porcelain dental restoration having a metal foil substrate.

It is another object of the present invention to provide an improved thin metal foil substrate-porcelain dental restoration.

It is yet another object of the present invention to provide a method of making a metal-porcelain dental restoration which utilizes, in-part, conventional techniques and materials used in making a metal foil matrix-porcelain dental restoration wherein the metal foil matrix is removed prior to placement of the restoration.

It is a further object of the present invention to provide an economical metal foil substrate-porcelain dental restoration.

Another object of the present invention to provide a method of making a metal foil substrate-porcelain dental restoration whereby the thickness of the metal foil substrate can be easily modified as needed.

Further objects and advantages of the present invention will become apparent from the following detailed description of the invention when read in conjunction with the accompanying drawings.

BRIEF DESCRIPTION OF THE DRAWINGS

FIG. 1 is a side view of a die of the prepared tooth coated with a thin layer of spacer material;

FIG. 2 shows the step of positioning a metal foil around the die for forming the metal foil substrate of the jacket crown;

FIGS. 3–6 show the steps of shaping the foil about the die;

FIG. 7 shows the step of trimming the foil after it has been configured to the die;

FIG. 8 shows the step of placing a sealing material within the portion of the foil to be terminated with a mechanical joint;

FIG. 9 shows the foil after it has been adapted, trimmed and finished;

FIG. 10 is a cross-sectional view along line 10—10 of FIG. 9 of the adapted and finished foil showing the mechanical joint and the sealing material contained therein;

FIG. 11 is an exploded perspective view of the die of FIG. 1 having first and second adapted, trimmed, and finished foils thereon.

FIG. 12 shows a die of a molar prepared tooth having a thin coating of spacer material thereon;

FIG. 13 shows an alternate embodiment of the present invention and the step of adapting a first metal foil to the occlusal surface and a portion of the axial surface of a molar toot die;

FIG. 14 shows the step of removing the first foil from the die and trimming the axial portion of the foil above the margin;

FIG. 15 shows the further step of positioning a second piece of metal foil about the die for adaptation to the axial surfaces thereof;

FIGS. 16-18 are side, lingual, and lingual views, respectively, which show the steps of adapting the second foil to the die;

FIG. 19 shows the second metal foil on the die after it has been adapted, trimmed and finished;

FIG. 20 shows a further step wherein the second foil has been removed from the die and the first foil has been replaced on the die and is in the process of receiving a sheet of sealing material thereon;

FIG. 21 shows a further step in the alternate embodiment wherein the finished second foil is replaced on the die over the first foil;

FIG. 22 shows the first and second foils of the alternate embodiment together in a substantially finished state;

FIG. 23 is an exploded perspective view showing another embodiment of the alternate embodiment of the present invention wherein another piece of foil adapted to the axial surfaces of the tooth is placed over the primary foil substrate;

FIG. 24 is a plan view of a strip of foil segmented to form the starting material for the metal foil show in FIG. 2.

FIG. 25 is a plan view of a strip of foil segmented to form the starting material for the axial metal foil shown in FIG. 15.

FIG. 26 is a plan view of a strip of foil segmented to form the starting material for the occlusal foil shown in FIG. 13.

FIG. 27 is a vertical sectional view showing a crown restoration having a foil core and porcelain veneer in accordance with the present invention.

DETAILED DESCRIPTION OF THE PREFERRED EMBODIMENT

The first embodiment of a method of making a dental crown in accordance with the principles of the present invention is shown in FIG. 11. FIG. 1, it is seen that the metal-porcelain restoration is fabricated by using a removable die 10, having a configuration capable of supporting and holding in position a dental restoration, as a temporary support during the formation of the crown.

The die 10 is usually a replica of the tooth to be replaced and is constructed by using techniques well known in the art. The die 10 will usually have a post portion 12, a base portion 14 and it can have an intermediate shoulder portion therebetween. Die 10 is useful for interior and premolar restorations.

A spacer coating 20 is applied by spraying or brush to post 12 to provide a space between post 12 and the interior configuration of the dental restoration being formed to facilitate matching the interior configuration of the restoration to the exterior of the tooth being restored. The coating may be a lacquer, acrylic liquid, rubber, paint or the like or a combination thereof. Preferably the coating 20 comprises two layers, the first layer being a suitable paint applied to a thickness of approximately 30 microns and the second layer being an air-dry liquid plastic coating such as that manufactured by PDI, Inc. as "Plasti Dip" understood to be described in U.S. Pat. No. 4,536,454 applied to a thickness of approximately 20 microns. The coating 20 is desired to have a relatively uniform thickness of about 50 microns and does not become a part of the finished restoration. The coating 20 is applied to substantially the entire surface of the die post 12 starting at a position approximately about 1 millimeter above the margin 16.

As shown best in FIGS. 2-7 and 24, a generally parallelogram shaped piece of thin metal foil 30 is adapted to post 12. The metal foil 30 is preferably composed of high fusing temperature metal which can withstand the bonding and curing temperatures utilized during formation of the crown without being deformed thereby. The foil 30 is preferably composed of platinum and is relatively thin preferably having a thickness around 25 microns (0.001 inch).

As shown in FIGS. 2-7, in accordance with conventional techniques well known in the art, the foil 30 is positioned about the die 10 so that a tinner's joint 40 can be formed on the proximal surface farthest from an adjacent tooth. FIGS. 3-7 demonstrate manual swaging of the foil 30 around the coated post 12 in the conventional manner for forming a foil matrix for a jacket crown wherein the matrix is removed prior to placement of the crown in the patient's mouth. In this regard, in FIG. 3 the ends 32 and 34 of the foil 30 are placed around the die 12 to roughly adapt the foil 30 to the die. As shown in FIG. 4, the ends 32 and 34 are pulled and squeezed away from the die to improve the gingival adaption.

As shown in FIG. 5, while the ends 32 and 34, are held away from the die, foil 30 is more closely adapted to the die 12 using a swaging implement 36. As shown in FIG. 6 the ends, 30 and 34 are drawn close against the proximal surface of the die 12 using a pliers 38. As shown in FIG. 7, a scissors 40 is used to trim excess foil to provide sufficient, such as approximately a one-three millimeter, flap 42 of foil parallel to the die on the proximal and incisal surfaces, to form a mechanical joint. The facial leaf 44 and lingual leaf 46 of flap 42, optionally, can be opened and the proximal and incisal parts of the lingual leaf 46 shortened if necessary to facilitate formation of a mechanical joint.

In accordance with prior conventional techniques of forming a jacket crown wherein the foil matrix would be removed prior to placement of the crown in the patient's mouth, at this stage foil 30 would be readapted to die 12 and a tinner's joint would be formed by folding facial leaf 44 over lingual leaf 46 and thereafter folding both leaves over again lingually. In accordance with the present invention, however, prior to forming a mechanical joint 47, a sealing material 48 is placed in between flaps 44 and 46. The sealing material 48 can be any suitable sealant but preferably is metal based, more preferably noble metal based, having a relatively low fusing temperature compared to the fusing temperature of the foil 30, which can be used as a solder to completely seal the mechanical tinner's joint without adversely affecting the structure of the foil 30. Commercial dental gold based compositions, such as Ceramco Inc.'s "Gold Genie" composition, used to repair pin holes, pitting or surface irregularities on gold alloy surfaces can also be appropriately formulated and used as the sealant 48. Preferably, the sealing material 48 is sponge gold or gold foil. As shown in FIGS. 8–10 and in accordance with the present invention, a mechanical joint 47 is made with the leaves 44 and 46 with the sealing material 48 therebetween. Preferably, the foil 30 is thereafter further adapted to the die by additional swaging to form a crown substrate 50.

The crown substrate 50 is removed from the die and heat is applied to completely seal the joint 47. In this regard, when the sealant 48 is gold, the substrate 50 can be fired by placement over a laboratory torch or bunsen burner for between five to thirty seconds based on flame temperature until the substrate 50 gets cherry red and shiny. Alternatively, the substrate 50 can be placed in a furnace and sintered at a temperature of about 1020° to 1070° C. until the same result is achieved to effect sealing of the joint. After sealing the joint 47, the substrate 50 is allowed to cool and thereafter the substrate is trimmed to completely cut the margin area.

According to the present invention, optionally, the thickness of the substrate 50 can be increased by additional layers of foil 30. In this regard, the additional layers of the foil 30 can be adapted to the die in accordance with the foregoing procedure. It, however, has been found that when additional layers of foil are utilized it is not necessary to seal the mechanical joint of each layer as demonstrated in FIG. 8 above.

Preferably, each additional substrate foil layer is adapted so that its terminal joint does not coincide with the terminal joint of any other substrate foil layer. In this regard, when two layers of foil are used to form the substrate, preferably, the terminal joints are on opposing sides of the restoration. Preferably each sequential layer of foil is bonded to the underlying layer of foil to form an integrated substrate. It has been found that successive layers of foil can be effectively bonded together by the use of sponge gold or gold foil therebetween as a bonding agent and appropriately firing thereafter. In this regard, preferably, a piece of gold foil is placed over the substrate 50 on the die prior to formation of the second layer of foil and the gold foil is conformed to the die during the adaptation of, and along with, the second layer of foil to the die. Preferably, the gold foil overlies the entire surface of the post 12. More preferably, the gold foil is configured so that during adaptation of the second substrate layer a portion of the gold foil will lie in between the leaves of the flap of the second substrate layer used to form its terminal joint. In such event, the second substrate layer can be terminated with a simple fold-over of the leaves rather than a more secure mechanical joint such as a tinner's joint. The multiple substrate layers with sufficient bonding agent therebetween are appropriately heated to bond the substrate layers into an integral substrate. The integral substrate is allowed to cool and the margin is again adjusted. Optionally, all margin cutting can be done at this time rather than in multiple steps.

FIG. 11 shows an exploded view of an integral substrate 60 comprised of a primary substrate layer 50 and a secondary substrate layer 55. As shown in FIG. 11, the joint 47 of the substrate layer 50 is preferably oriented opposite to the joint 61 of the substrate layer 60 (shown in phantom).

After formation, the exterior surface of the crown foil substrate preferably is cleaned such as by sandblasting, steam cleaning or ultrasonic treatment. As shown in FIG. 27, a porcelain restoration incorporated the finished substrate 50 can be prepared by directly applying conventional dental porcelain compositions to the substrate to form the jacket crown of the present invention. Preferably a conventional retention coating 65 is applied to the entire exterior surface of the foil substrate to enhance the bonding of porcelain to the substrate. Preferably, the retention coating is gold colored to facilitate formation of a properly colored porcelain finish. Sponge gold or gold foil can be applied and fired as a retention coating. It has been found that a dental bonding composition manufactured by Degusa Company under the name Blendgold when applied and fired according to the manufacture's suggestion directions provides excellent results as a retention coating to enhance the bonding of the porcelain to the substrate. Any number of porcelain layers 67 may be applied and fired for forming the jacket crown of the invention. Generally, three or more layers of varying dental porcelain compositions starting with an opaque layer are built-up and fired at temperatures generally specified by the manufacturer of the composition selected. These temperatures generally start at about 600° C. with final firing temperatures ranging from about 900° C. to approximately 1050° C. for aluminus core compositions. Thereafter, the porcelain crown is finished and corrected for final insertion in the mouth according to standard techniques.

Depending upon the degree of shrinkage of the substrate structure resulting from application and firing of the porcelain core, it may be necessary to remove a portion or all of spacer coating 20 to properly reseat the substrate 50 on the die 10. Preferably, as discussed above, the spacer coating 20 is comprised of two layers including an about 30 micron paint base layer and an about 20 micron readily removable plastic secondary layer which secondary layer may be removed to facilitate reseating of the substrate 50 on the die 10 covered with the paint base coat for further build-up or other work.

Referring generally to FIGS. 12–23, an alternate embodiment of a metal-porcelain restoration of the present invention useful for molar restorations is shown. Referring to FIG. 12, molar metal-porcelain restorations of the present invention can be fabricated by using a removable die 70 having a configuration capable of supporting and holding in position a dental restoration. The die 70 is usually a replica created from an existing tooth using techniques well known in the art. The die 70 will usually have a post portion 72, a base portion 74 and and it can have an intermediate shoulder portion therebetween. Preferably, prior to using the die 70 for formation of the dental restoration, the post 72 is coated with a spacer coating 20 as described above.

As shown in FIGS. 13 and 26, a generally rectangular shaped piece of high fusing temperature foil 80 is adapted to the occlusal surface and a portion of the axial surface of the post 72. The foil 80 is preferably composed of platinum and is relatively thin preferably having a thickness around 25 microns (0.001 inch). The foil 80 can be adapted to the post 72 by conventional manual swaging of the foil using finger pressure and a swaging implement. As shown in FIG. 14 after the foil 80 has been adapted to the occlusal surface and a portion of the axial surface of the post 72, the foil 80 is removed from the die 70 and any axial portion of the foil 80 close to or below the margin 76 is trimmed away.

As shown in FIGS. 15-19 and 25, a generally chevron shaped piece of high fusing temperature metal foil 84 is adapted to the axial surfaces of post 72. The foil 84 is preferably composed of platinum and is relatively thin preferably having a thickness about 25 microns (0.001 inch). Preferably the foil 84 is positioned about the die 70 for adaption to the axial surfaces of the post 72 in such a manner whereby the foil 84 can be terminated by a single mechanical joint on the lingual side of the die 70. In this regard, the foil 84 is positioned relative to the die 70 so that the ends 86 and 88 of the foil 84 can be pulled around the post 72 and joined on the lingual side of the post 72. As shown in FIG. 16, the ends 86 and 88 are pulled around and squeezed away from the die 70 to improve the gingival adaption. Similar to the techniques shown in FIGS. 4-6 above, while the ends 86 and 88 are held away from the die, the foil 84 is more closely adapted to the die 70 using a swaging implement and pliers. As shown in FIG. 17, a scissors 40 is used to trim excess foil from the ends 86 and 88 to provide sufficient, such as approximately a one-three millimeter, flap 90 of foil on the lingual side of the die 70. Optionally, either leaf 92 or 94 of the flap 90 can be shortened relative to the other leaf to facilitate formation of a mechanical joint therebetween by folding the longer leaf over the shorter leaf and thereafter folding both leaves over again.

As shown in FIG. 18, a sealing material 96 is placed in between the leaves 92 and 94 prior to termination of the foil 84. The sealing material 96 can be any suitable sealant but preferably is metal based, more preferably noble metal based, having a relatively low fusing temperature compared to the fusing temperatures of the metal comprising the foils 80 and 84 and can be used as a solder to completely seal the ends 86 and 88. Commercial dental compositions, such as Ceramco Inc.'s "Gold Genie" composition, used to repair pin holes, pitting or surface irregularities on gold alloy surfaces can also be appropriately formulated and used as the sealant 96. Preferably, the sealing material 96 is sponge gold or gold foil. In accordance with the present invention, a mechanical joint 98 is made with the leaves 92 and 94 with the sealing material 96 therebetween. Preferably, the foil 84 is thereafter further adapted to the die by additional swaging. The adapted foil 84 is then removed from die 70.

As shown in FIG. 20, the adapted foil 80 is then replaced on post 72. Sealing material 100 is placed over at least the axial portion of the foil 80. In this regard, the sealing material 100 can be the same as or different from the sealing material 96. Preferably, the sealing material 100 is thin gold foil which can be used as a solder to, as described hereinafter, join and seal the foil 80 to the foil 84. Preferably, the sealant 100 is adapted to generally conform to the occlusal and axial surface of the foil 80. As shown in FIG. 21, the adapted facial foil 84 is replaced on the die over the sealant 100 and the occlusal foil 80. The occlusal foil 80, the facial foil 84 and the sealant 100 are thereafter further adapted to the die by swaging. Preferably, the occlusal foil 80, the facial foil 84 and the sealant 100 are swaged sufficiently to form a unitary structure 102.

The unitary structure 102 is removed from the die and heat is applied to seal the joint 98 and to seal the occlusal foil 80 and the facial foil 84 to one another. In this regard, appropriate materials and means are utilized and the occlusal foil 80 and the facial foil 84 have been formed with sufficient overlap therebetween to insure such sealing. When the sealant 96 and the sealant 100 are both gold, the unitary structure 102 can be fired by placement over a laboratory torch or bunsen burner for between 5 to 30 seconds based on flame temperature until the unitary structure 102 gets cherry red and shiny. Alternatively, the unitary structure 102 can be placed in a furnace and sintered at a temperature of about 1020° to 1070° C. until the same result is achieved to effect sealing. Thereafter, the unitary integrated structure 102 is allowed to cool and is trimmed to adjust the margin as desired. It will be appreciated, that modifications to the foregoing method can be performed such as adapting the facial foil 84 in the presence of the occlusal 80. In this regard, the occlusal foil 80 could be adapted to the die, the sealant 100 could be applied and the facial foil 84 could be adapted to the die about the occlusal foil 80 and the sealant 100.

According to the present invention, optionally, the thickness of the unitary integrated structure 102 can be increased by additional layers of foil. In this regard, it has been found that the thickness of the integrated structure 102 can be satisfactorily increased by additional layers of facial foil 84 without additional layers of occlusal foil 80. It has also been found that when additional layers of foil are utilized, it is not necessary to seal the mechanical joint of each layer as shown in FIGS. 18 and 19 and discussed hereinabove.

Preferably, each additional substrate foil layer is adapted so that its terminal joint does not coincide with the terminal joint of any other substrate foil layer. For aesthetic reasons, preferably the terminal joint of each foil layer is lingually, mesially or distally oriented.

Preferably, each sequential layer of foil is bonded to the underlying layer of foil to form an integrated substrate. It has been found that successive layers of foil can be effectively bonded together by the use of sponge gold or gold foil as a bonding agent therebetween and appropriately firing thereafter. In this regard, preferably, a piece of gold foil is placed over the unitary integrated substrate 102 on the die prior to formation of the second layer of foil and the gold foil is conformed to the die during the adaptation of, and along with, the second layer of foil to the die. Preferably, the gold foil surrounds the entire radial circumference of the substrate 102. More preferably, the gold foil is configured so that during adaptation of the second substrate layer a portion of the gold foil will lie in between the leaves of the flap of the second substrate layer used to form its terminal joint. In such event, the second substrate layer can be terminated with a simple fold-over of the leaves rather than a more secure mechanical joint such as a tinner's joint. The multiple substrate layers with a bonding agent therebetween are appropriately heated to bond the substrate layers into an integral substrate. The integral substrate is allowed to cool and the margin is again adjusted. Optionally, all margin cutting can be done at this time rather than in multiple steps.

FIG. 23 shows an exploded view of an integral substrate layer 102 and a secondary substrate layer 104. As shown in FIG. 23, the joint 98 of the substrate layer 102 and the joint 106 of the substrate layer 104 are both lingually oriented in a non-overlapping manner. After formation of the molar metal foil substrate is completed, porcelain or another veneering material can be built thereupon as described above. In this regard, preferably the exterior surface of the molar crown foil substrate is cleaned such as by sandblasting, steam cleaning or ultrasonic treatment. Preferably a conventional retention coating is applied to the entire exterior surface of the foil substrate to enhance the bonding of porcelain to the substrate. Any number of porcelain layers may be applied to the posterior foil substrate for forming the jacket crown of the invention.

What is claimed is:

1. A method of forming a dental jacket crown comprising the steps of:
    (a) preparing a die of a prepared tooth;
    (b) adapting a thin metal foil having at least two ends to the die to conform the foil to the die, said foil being composed of high fusing temperature metal;
    (c) orienting and manipulating said two ends so that a mechanical joint can be formed therebetween;
    (d) positioning a soldering material having a fusing temperature lower than the fusing temperature of said metal foil within said two ends oriented to form a mechanical joint;
    (e) manipulating said metal foil two ends to form the mechanical joint;
    (f) heating said foil two ends to a temperature above the low fusing temperature of said soldering material and below the fusing temperature of the high fusing metal foil to seal said mechanical joint;
    (g) coating said foil with a veneering material.

2. The method of claim 1 wherein said metal foil is composed of platinum.

3. The metal of claim 1 wherein said soldering material is gold foil.

4. The metal of claim 1 wherein said mechanical joint is a tinner's joint.

5. The method of claim 1 wherein said mechanical joint is formed along a proximal surface of the restored tooth.

6. The method of claim 1 further including the steps of providing a second thin metal foil of high fusing temperature metal, placing said second foil about said adapted and terminated metal foil and adapting the shape of said second foil to said dye prior to said step of coating of veneering material.

7. The method of claim 6 including the step of terminating said second metal foil in a mechanical joint.

8. The method of claim 7 wherein said joint of said second foil is oriented so as not to overlie said joint of said foil.

9. The method of claim 8 wherein said second joint is oriented relatively opposite to the position of said joint of said first metal foil.

10. The method of claim 6 further including the steps of placing a bonding material between said foil and said second foil to bond said second foil and said foil together to form into an integral structure.

11. The method of claim 10 wherein said bonding material comprises gold.

12. The method of claim 11 wherein said bonding material is gold foil.

13. The method of claim 1 further including the step of coating said die with a thin layer of spacer material prior to adapting said metal foil thereto.

14. A dental crown made in accordance with the method of claim 1.

15. A method of forming a dental jacket crown comprising the steps of:
    (a) preparing a die of a posterior prepared tooth;
    (b) adapting a first thin metal foil of high fusing temperature metal to the die to conform to the occlusal surface and to a portion of the axial surface of the prepared tooth;
    (c) removing said first foil from the die;
    (d) adapting a second thin metal foil of high fusing temperature metal to the die to conform to the axial surfaces of the prepared tooth and orienting said second foil in a manner to permit same to be terminated in a mechanical joint;
    (e) positioning a soldering material having a fusing temperature lower than the fusing temperature of said second metal foil within the portion of said foil oriented to form a mechanical joint;
    (f) manipulating said second foil to form a mechanical joint;
    (g) removing said second foil from the die;
    (h) replacing the first adapted foil to the die;
    (i) placing a bonding material having a bonding temperature lower than the fusing temperatures of said first and second metal foils over at least a portion of the axial surface of said first foil;
    (j) replacing said second foil on the die over said first foil and said bonding material;
    (k) heating said adapted foils at a temperature above the low fusing temperatures of said soldering material and said bonding material to seal said mechanical joint and to bond said second metal foil and said first metal foil into an integral structure;
    (l) coating said integral structure with a veneering material.

16. The method of claim 15 wherein the surface of the die is coated with a thin layer of spacer material prior to adapting said metal foils to said die.

17. The method of claim 15 wherein said soldering material and said bonding material are composed of the same material.

18. The method of claim 15 wherein said soldering material comprises gold.

19. The method of claim 15 wherein said bonding material comprises gold.

20. The method of claim 19 wherein said bonding material is gold foil and said gold foil also overlies the occlusal surface of said first foil.

21. A dental crown made in accordance with the method of claim 15.

22. A method of forming a dental jacket crown comprising the steps of:
    (a) adapting a first thin metal foil composed of high fusing temperature metal to a tooth die, said tooth die having occlusal and axial surfaces, to conform said first foil to the occlusal surface and at least to a portion of the axial surfaces of said die to form a generally cup shaped foil cap for said die;
    (b) adapting a second thin metal foil composed of high fusing temperature metal to conform to the axial surfaces of said die and to form a facial sleeve for said die;

(c) joining said facial sleeve to said cap to form a unitary substrate structure generally conforming to the tooth die; and (d) coating said integral structure with a veneering material.

23. The method of claim 22 wherein said first foil and said second foil are composed of platinum.

24. The method of claim 22 further including the step of providing said facial sleeve with a sealed joint.

25. A dental crown made in accordance with the method of claim 22.

* * * * *